US00PP32699P3

(12) United States Plant Patent
Randag

(10) Patent No.: US PP32,699 P3
(45) Date of Patent: Dec. 22, 2020

(54) CALLA LILY PLANT NAMED 'DOZANMACA'

(50) Latin Name: *Zantedeschia sprengeri*
Varietal Denomination: Dozanmaca

(71) Applicant: Dümmen Group B.V., De Lier (NL)

(72) Inventor: Cecilius Jan-Jochem Randag, CJ 'T Zand (NL)

(73) Assignee: Dümmen Group B.V., De Lier (NL)

( * ) Notice: Subject to any disclaimer, the term of this patent is extended or adjusted under 35 U.S.C. 154(b) by 0 days.

(21) Appl. No.: 16/602,412

(22) Filed: Sep. 30, 2019

(65) Prior Publication Data

US 2020/0113100 P1 Apr. 9, 2020

Related U.S. Application Data

(60) Provisional application No. 62/766,205, filed on Oct. 4, 2018.

(51) Int. Cl.
*A01H 5/02* (2018.01)
*A01H 6/10* (2018.01)

(52) U.S. Cl.
USPC ..... Plt./490
CPC ..... *A01H 6/10* (2018.05)

(58) Field of Classification Search
USPC ..... Plt./490
CPC ..... A01H 5/02
See application file for complete search history.

*Primary Examiner* — Kent L Bell
(74) *Attorney, Agent, or Firm* — The Webb Law Firm

(57) ABSTRACT

'Dozanmaca' is a new variety of calla lily plant having dark purple colored spathes that produces 3-14 inflorescences per 14-16 cm tuber. The flower stems are about 30-40 cm in height. The leaves are green with a greyed-purple margin and have a leathery texture.

1 Drawing Sheet

Botanical classification: *Zantedeschia sprengeri*.
Varietal denomination: 'Dozanmaca'.

BACKGROUND OF THE NEW PLANT

The present invention comprises a new and distinct cultivar of calla lily, botanically known as *Zantedeschia sprengeri* and hereinafter referred to by the cultivar name 'Dozanmaca', but having an original cultivar name of 'Macau'.

'Dozanmaca' is a product of a planned breeding program, which had the objective of creating *Zantedeschia* hybrids for pot flower production in a wide range of colors with a large, classic flower shape. The breeding program began in 1989, and the new cultivar is a seedling selected from the crossing of *Zantedeschia sprengeri* seedling Z041583 (female parent, unpatented) with *Zantedeschia sprengeri* variety 'Allure' (male parent, unpatented). 'Dozanmaca' was selected in 2012 by the inventor in 't Zand, The Netherlands as one flowering plant within the progeny of the stated cross.

The first act of asexual reproduction of 'Dozanmaca' by tissue culture was performed by the inventor in September of 2014 in 't Zand, The Netherlands. Subsequent asexual reproductions by tissue culture at the same location have demonstrated that the combination of characteristics as herein disclosed for the new cultivar are retained and reproduced true to type through successive generations of asexual reproduction.

The following observations, measurements and comparisons describe plants grown from 12 to 14 weeks in 14 cm pots in 't Zand, The Netherlands under greenhouse conditions, which approximate those generally used in horticultural practice. Color references are made to The 2001 R.H.S.

Colour Chart of The Royal Horticultural Society of London, 4$^{th}$ Edition, except where general color terms of ordinary significance are used.

The present invention has not been evaluated under all possible environmental conditions. The phenotype may vary with variations in environment without a change in the genotype of the plant.

The following traits have been repeatedly observed and determined to be basic characteristics of 'Dozanmaca' which, in combination, distinguish this calla lily as a new and distinct cultivar:

1. Numerous, small, and dark purple colored spathes;
2. Greyed-purple leaf margin; and
3. Highly contrasting yellow colored spadix.

Table 1 provides a comparison of 'Dozanmaca' to its parents, as well as *Zantedeschia sprengeri* variety 'Black Star' (U.S. Plant Pat. No. 14,844).

TABLE 1

| Variety | Relationship | Trait differences | Description |
|---|---|---|---|
| 'Dozanmaca' | New variety | Spathe color | Upper surface is RHS 187A |
| | | Plant height | 30-42 cm |
| Z041583 | Female parent | Spathe color | Varies between RHS N186C and N186D |
| | | Plant height | 39-51 cm |
| 'Allure' | Male parent | Spathe color | Varies between RHS 59A and 59B |
| | | Plant height | 30-42 cm |
| 'Black Star' | Known variety | Spathe color | Upper surface is between RHS 187A and RHS 202A |
| | | Plant height | 60-75 cm |

BRIEF DESCRIPTION OF THE DRAWING

The accompanying photographic drawing illustrates the new variety, with the colors being as nearly true as is possible with color illustrations of this type.

DESCRIPTION OF THE NEW PLANT

Type: Deciduous.

Size:

*Height of the leaf canopy above the soil.*—38-42 cm.

*Height of top of inflorescences above the soil.*—30-40 cm.

*Diameter.*—42-59 cm.

Form: Upright.

Number of inflorescences per tuber:

*Size* 14-16 *cm in diameter.*—3-14 inflorescences.

Branches:

*Number.*—Plentiful.

*Color.*—Greyed-Purple Group RHS 187C.

*Young shoot color.*—Greyed-Purple Group RHS N186C.

Leaves:

*Size.*—Width: 6-8 cm, with the broadest part of the leaf blade in the middle. Length: 20-24 cm.

*Number per plant.*—45-60.

*Leaf blade lobes.*—Absent.

*Shape.*—Lanceolate.

*Apex.*—Apiculate.

*Base.*—Attenuate.

*Margin.*—Entire; having a color of Greyed-Purple Group RHS 187A.

*Color.*—Upper surface: Green Group RHS 137B, with Greyed-White Group RHS 156D maculations present. Lower surface: Green Group RHS 137B, with White Group RHS N155A maculations present.

*Veins.*—Configuration: Pinnate. Color: Green Group RHS 143A.

*Surface texture.*—Smooth (both surfaces).

*Petiole.*—Length: 18-21 cm. Diameter: Average of 30 mm. Color: The base is Greyed-Purple Group RHS 187C, the upper part is Greyed-Purple Group RHS 187C.

Roots:

*Color.*—White Group RHS 155C.

*Branching description.*—Fibrous root system. Several main roots emerge from the top of the tuber and form a small number of lateral roots.

Spathe:

*Size.*—Length (measured from opening to tip): 6.5-8 cm. Width: 3-4 cm. Height: 8-11 cm.

*Color.*—Throat spot: Absent. Upper surface: Greyed-Purple Group RHS 187A. Lower surface: Greyed-Purple Group RHS 187A.

*Vein color.*—Greyed-Purple Group RHS 187A.

*Shape.*—Cupped.

*Apex.*—Caudate.

*Base.*—Attenuate.

*Margin.*—Entire.

Spadix:

*Shape.*—Cylinder.

*Size.*—Length: 25-30 mm. Diameter: 10-15 mm.

*Color.*—Yellow-Orange Group RHS 15B to 15C.

*Position relative to spathe.*—Upright.

*Female flower.*—Number: 20-40. Shape: Pyramid. Height: 2 mm. Diameter: 3.5 mm.

*Male flower.*—Number: 220-280. Shape: Cone. Height: 1.5 mm. Diameter: 0.2 mm.

Peduncle:

*Size.*—Length: 26.5-34 cm. Diameter: 15-20 mm.

*Color.*—The upper part is Greyed-Purple Group RHS 187C, the lower part is Greyed-Purple Group RHS 187C.

*Texture.*—Smooth.

Reproductive organs:

*Location of female organs.*—Basal position of the spadix.

*Location of male organs.*—Upper position of the spadix.

*Perianth.*—Conspicuous.

*Stamens.*—Presence: Not visible before pollen release. Number: Between 480 and 600. Pollen amount: Abundant; similar to 'Picasso' (U.S. Plant Pat. No 15,282). Color: Between White Group RHS 155B and 155C.

*Anther.*—Shape: Round. Length: Less than 1 mm. Color: Between Yellow Group RHS 8B and 8C.

*Filament.*—Length: Less than 1 mm. Color: White Group RHS 155D.

*Pistils.*—Number: 15 to 30. Length beyond perianth: About 1 mm.

*Stigma.*—Shape: Round. Size: Less than 1 mm.

*Style.*—Length: Less than 1 mm. Color: Between Yellow Group RHS 8B and 8C.

*Ovaries.*—Texture: Smooth. Length: Between 1 to 10 mm. Width: Between 1 to 10 mm. Color: The top color is Yellow-Orange Group RHS 14D, the bottom color is Greyed-Purple Group RHS 183D.

Disease resistance: No unusual susceptibility/resistance to diseases noticed to date.

Pest resistance: No unusual susceptibility/resistance to pests noticed to date.

Heat tolerance: No heat tolerance.

Hardiness: Not hardy.

Flowering: In general, the time from planting to first flowering takes eight weeks.

Lastingness: About two weeks on the plant.

Fragrance: None.

I claim:

1. A new and distinct variety of calla lily plant named 'Dozanmaca' as herein described and illustrated.

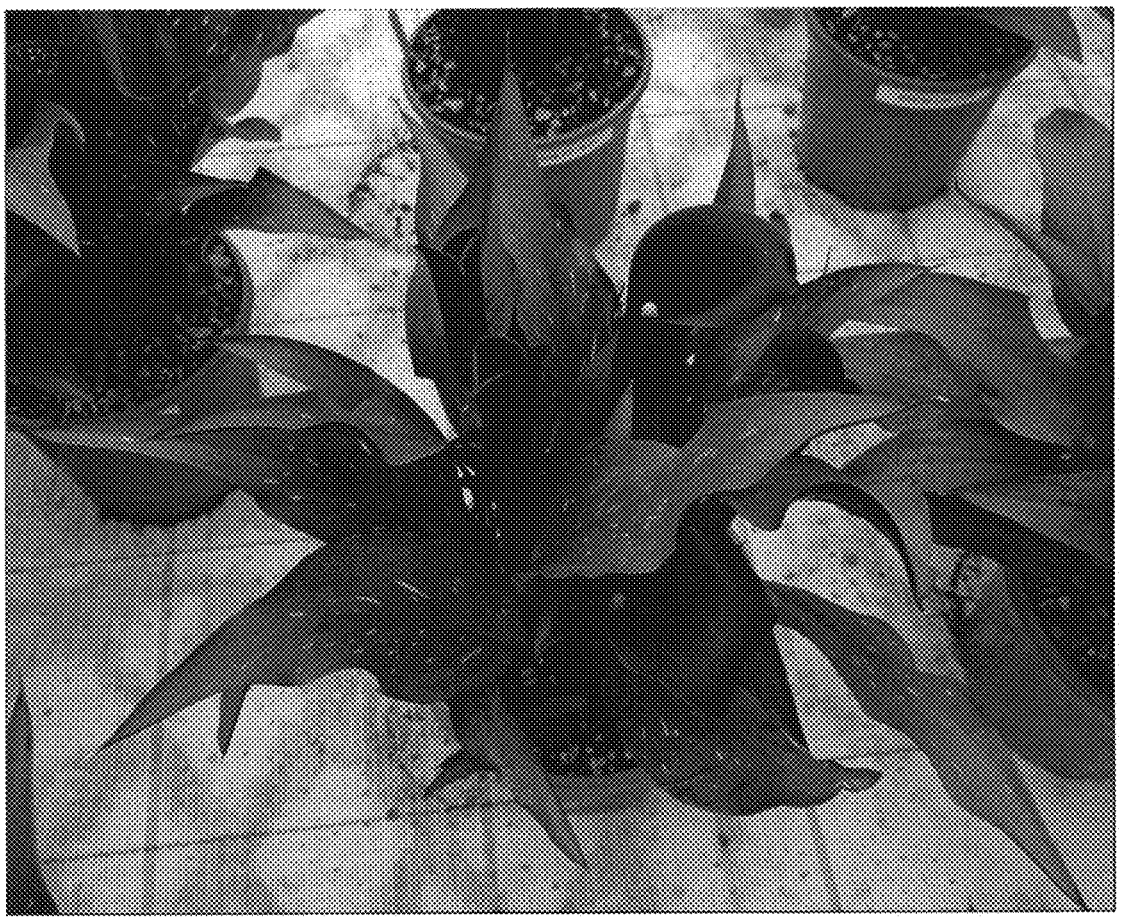

* * * * *